United States Patent [19]
Ogata et al.

[11] Patent Number: 5,474,991
[45] Date of Patent: Dec. 12, 1995

[54] LIPID METABOLISM IMPROVING MEDICINAL COMPOSITION

[75] Inventors: Kazumi Ogata, Toyonaka; Takahiro Sakaue, Itami; Yasuko Umegaki, Kobe; Rie Nagao, Neyagawa, all of Japan

[73] Assignee: Senju Pharmaceutical Co., Ltd., Osaka, Japan

[21] Appl. No.: 215,814

[22] Filed: Mar. 22, 1994

[30] Foreign Application Priority Data

Mar. 31, 1993 [JP] Japan .................. 5-073814

[51] Int. Cl.⁶ .............. A61K 31/665; C07F 9/06
[52] U.S. Cl. ............. 514/100; 514/824; 514/893; 514/909; 549/220
[58] Field of Search ............... 514/100, 824, 514/893, 909; 549/220

[56] References Cited

U.S. PATENT DOCUMENTS

| | | | |
|---|---|---|---|
| 4,564,686 | 1/1986 | Ogata | 549/220 |
| 4,888,329 | 12/1989 | Ogata et al. | 514/100 |
| 4,914,197 | 4/1990 | Yamamoto et al. | 514/100 |
| 4,948,786 | 8/1990 | Shimamoto et al. | 514/100 |
| 5,053,222 | 10/1991 | Takasu et al. | 514/100 |
| 5,098,898 | 3/1992 | Ogata et al. | 549/222 |
| 5,231,090 | 7/1993 | Hsia et al. | 514/824 |
| 5,306,713 | 4/1994 | Suetsugu et al. | 514/100 |
| 5,378,692 | 1/1995 | Ohmori et al. | 514/19 |

*Primary Examiner*—Ronald W. Griffin
*Attorney, Agent, or Firm*—Wenderoth, Lind & Ponack

[57] ABSTRACT

This invention relates to a lipid metabolism improving medicinal composition containing a phosphoric acid diester compound of the formula or a pharmacologically acceptable salt thereof.

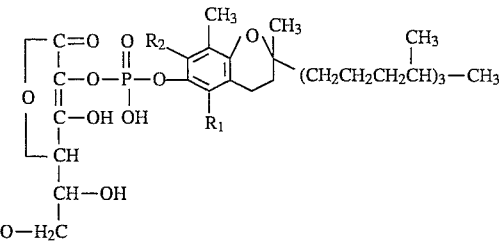

wherein $R_1$ and $R_2$ are the same or different and each represents a hydrogen atom or a methyl group.

The lipid metabolism improving medicinal composition of this invention lowers the plasma levels of triglycerides (TG), non-esterified fatty acids (NEFA), total cholesterol (T-ch), esterified cholesterol (E-ch), free cholesterol (F-ch), total lipid (TL) and lipid peroxides (LPO) and, among cholesterol fractions, increases the high-density lipoprotein (HDL) fraction and reduces the low-density ipoprotein (VLDL) fractions. Therefore, the composition can be used with advantage for the amelioration of hyperlipidemia associated with arteriosclerotic diseases such as myocardial infarction, angina pectoris, cerebral infarction, cerebral arteriosclerosis, etc., nephrosis, hypertension, diabetes, obesity and other diseases and for the prophylaxis of various cerebrovascular diseases.

1 Claim, No Drawings

LIPID METABOLISM IMPROVING MEDICINAL COMPOSITION

BACKGROUND OF THE INVENTION

1. Field of the Invention

This invention relates to a useful lipid metabolism improving medicinal composition. More particularly, this invention relates to a useful lipid metabolism improving medicinal composition containing an ascorbyl tocopheryl phosphate compound or a pharmacologically acceptable salt thereof.

2. Description of the Prior Art

Hyperlipidemia is generally considered to be a risk factor for arteriosclerosis. It is also known that arteriosclerotic changes occur as plasma lipids, particularly cholesterol, adhere to, and become deposited on, the arterial wall. Recent advances in research in this field have shown that an increase in low-density lipoprotein (LDL), among plasma lipids, plays a major role in the pathogenesis off arteriosclerosis, while high-density lipoprotein (HDL) contributes to the removal and decomposition of the cholesterol which has been deposited on the vascular wall and cell membrane, thus acting as an antiarteriosclerotic factor.

Therefore, with the view of treating and preventing hyperlipidemia, which may be of divergent etiologies, and of arteriosclerosis and other diseases associated with hyperlipidemia, efforts are being made to develop blood cholesterol-lowering drugs, particularly drugs which would reduce the low-density lipoprotein level and increase the high-density lipoprotein level in the blood.

Under the circumstances, the inventors of this invention explored for compounds having potent lipid metabolism-improving activity. As a consequence, the inventors discovered that certain ascorbyl tocopheryl diester compounds of phosphoric acid and their pharmacologically acceptable salts have meritorious lipid metabolism-improving activity, for example the action to reduce LDL and increase HDL effectively and, based on this finding, did further research to complete this invention.

SUMMARY OF THE INVENTION

This invention relates to a lipid metabolism improving medicinal composition containing a phosphoric acid diester compound of the following formula (hereinafter referred to as the present compound) or a pharmacologically acceptable salt thereof.

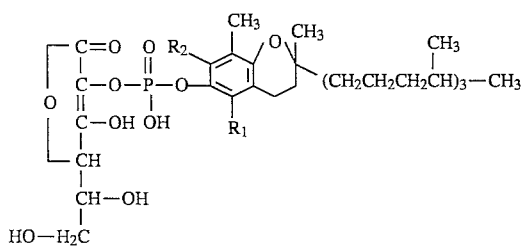

(wherein $R_1$ and $R_2$ are the same or different and each represents a hydrogen atom or a methyl group).

DETAILED DESCRIPTION OF THE INVENTION

The present compound to be used in the lipid metabolism improving medicinal composition of this invention can be synthesized by the processes described in, inter alia, Japanese Patent (JP) Publication Hei-2- 44478 and JP Hei-5-23274 or any processes analogous thereto.

The present compound for use in the lipid metabolism improving composition of this invention is already known to be of value as an anticataract drug, a prophylactic and therapeutic drug for climacteric disturbance, a skin-beautifying cosmetic (JP Publication Hei-2-44478), an anti-inflammatory drug (JP Publication Hei-1-27044), an antiulcer drug (JP Kokai S-63-27062) and a prophylactic and therapeutic agent for ischemic disorder in organs (JP Kokai Hei-2- 111722), for instance.

The present compound, as a lipid metabolism improving agent, can be employed for purposes of this invention regardless of whether it is the free acid form or a pharmacologically acceptable salt thereof. The salt may be an alkali metal salt such as the sodium salt and the potassium salt, or an alkaline earth metal salt such as the calcium salt and the magnesium salt. Any other salts, if pharmacologically acceptable, can also be employed.

The lipid metabolism improving medicinal composition of this invention may contain any one or, if necessary, more than one species of the present compound depending on the intended use and need.

The present compound as the active ingredient of the lipid metabolism improving medicinal composition of this invention is sparingly toxic and, therefore, safe clinically, wherefore it can be put to use with advantage [$LD_{50}$ of the monopotassium salt of phosphoric acid diester of L-ascorbic acid, DL-α-tocopherol (hereinafter referred to briefly as EPC-$K_1$) is $\geq 5$ g/kg p.o. (rats), $\geq 100$ mg/kg i.v. (rats)].

The lipid metabolism improving medicinal composition of this invention can be administered orally or parenterally for the treatment or prevention of hyperlipidemia due to various causes and of arteriosclerosis and other diseases associated with hyperlipidemia. It can be used in various dosage forms, e.g. solid preparations such as tablets, granules, powders, capsules, etc. and liquid preparations such as injections, all of which can be manufactured by established pharmaceutical procedures. These dosage forms may contain a variety of additives which are commonly employed, such as excipients, reabsorption promoters, buffers, surfactants, solubilizer, preservatives, emulsifiers, isotonizing agents, stabilizers, pH control agents, etc., each in a suitable amount or proportion.

The dosage of the present compound for use as a lipid metabolism improving agent is dependent on species of the present compound, type of diseases, patient's age, and body weight, therapeutic regimen, etc. but taking an injection as an example, about 1 mg to about 100 mg per adult man can be administered once a day and in the case of an oral preparation, about 10 mg to about 1,000 mg can be administered a few times a day.

The lipid metabolism improving medicinal composition of this invention may further contain, unless contrary to the object of the invention, one or more other lipid metabolism improving agents and/or other pharmacologically active ingredients.

EXAMPLES

The following experimental and working examples are further illustrative of this invention.

[Test Example 1] Effect of the present compound on high cholesterol diet-fed hyperlipidemic rats The effect of the present compound administered orally was evaluated in high cholesterol nicotinate, both of which are commercially available, as reference drugs.

[Test substances]

(1) L-Ascorbyl DL-α-tocopheryl phosphate monopotassium (EPC-$K_1$) 100 mg/kg and 200 mg/kg p.o. (dissolved in distilled water)

(2) Probucol 200 mg/kg p.o. (suspended in 0.5% CMC)

(3) Tocopherol nicotinate 200 mg/kg p.o. (suspended in 0.5% CMC)

[Methods]

Male SD rats purchased from Clea Japan were used (4 weeks of age). These animals were fed on a cholesterol (1%)-containing solid food (Nihon Nosan Kogyo K.K.) to construct rat models of hyperlipidemia. The test substance was administered once a day for 12 days. On the 12th day, blood samples were collected for the determination of total lipid (TL), phospholipids (PL), triglycerides (TG), total cholesterol (T-ch), free cholesterol (F-ch), esterified cholesterol (E-ch), non-esterified fatty acids (NEFA), lipid peroxides (LPO), HDL-cholesterol (HDL-ch), β-lipoprotein (β-LP) and lipoprotein fractions. Normal solid food (Nihon Nosan Kogyo K.K.) was supplied to rats in the normal group.

[Results]

The results are shown in Table 1. It is apparent from Table 1 that the present compound at 200 mg/kg significantly lowered total cholesterol (T-ch), free cholesterol (F-ch), esterified cholesterol (E-ch) and lipid peroxide levels. Moreover, the present compound lowered total cholesterol (T-ch), free cholesterol (F-ch), esterified cholesterol (E-ch) and total lipid (TL) by the same degrees as did 200 mg/kg of probucol and 200 mg/kg of tocopherol nicotinate.

The effect of the present compound administered orally was compared with that of probucol in rats with streptozotocin-induced hyperlipidemia.

[Test substances]

EPC-$K_1$ 125 and 250 mg/kg (dissolved in distilled water)

Probucol 125 mg/kg (suspended in 0.5% CMC)

[Method]

Streptozotocin 50 mg/kg was injected into the tail vein of Wistar rats (4-week-old) to induce hyperglycemia and hyperlipidemia. Blood samples for biochemical tests were collected 24 hours after administration of streptozotocin. The test substance was administered orally 1 hour before administration of streptozotocin.

[Results]

The results are shown in Table 2. As apparent from Table 2, the present compound at 125 and 250 mg/kg caused significant decreases in triglycerides (TG), lipid peroxides (LPO), non-esterified fatty acids (NEFA) and total lipid (TL). Referring to cholesterol fractions, the present compound caused an overt increase in high-density lipoprotein (HDL) and overt decreases in low-density lipoprotein (LDL) and very-low-density lipoprotein (VLDL). Probucol 125 mg/kg lowered triglycerides (TG), non-esterified free acids (NEFA) and total lipid (TL) by substantially the same degrees as the present compound did but elevated the very-low-density lipoprotein (VLDL) level and failed to lower lipid peroxides (LPO).

TABLE 1

| Group | Control | EPC-$K_1$ | | Probucol | Tocopherol nicotinate | Normal |
|---|---|---|---|---|---|---|
| Dose (mg/kg) | group | 100 | 200 | 200 | 200 | group |
| Triglycerides | 45 ± 17 | 50 ± 20 | 49 ± 14 | 43 ± 14 | 39 ± 17 | 82 ± 24 |
| Total cholesterol | 307 ± 89 | 257 ± 72 | 239 ± 59*[1] | 240 ± 40*[1] | 247 ± 50 | 75 ± 10 |
| Free cholesterol | 54 ± 18 | 44 ± 13 | 40 ± 13*[1] | 38 ± 8*[2] | 42 ± 10*[1] | 12 ± 2 |
| Esterified cholesterol | 251 ± 73 | 213 ± 60 | 198 ± 47*[1] | 202 ± 32*[1] | 205 ± 41 | 63 ± 8 |
| HDL-ch | 28 ± 7 | 29 ± 7 | 29 ± 4 | 29 ± 5 | 32 ± 6 | 45 ± 4 |
| β-Lipoprotein | 726 ± 184 | 633 ± 157 | 608 ± 145 | 598 ± 101 | 602 ± 109 | 190 ± 37 |
| LDL | 227 ± 131 | 238 ± 67 | 256 ± 94 | 274 ± 99 | 304 ± 61 | 169 ± 40 |
| VLDL | 597 ± 326 | 491 ± 268 | 416 ± 237 | 381 ± 154*[1] | 368 ± 174*[1] | 5 ± 3 |
| Free fatty acids | 1116 ± 331 | 1115 ± 312 | 1139 ± 353 | 1249 ± 284 | 1041 ± 150 | 725 ± 192 |
| Phospholipids | 180 ± 29 | 174 ± 19 | 172 ± 17 | 168 ± 15 | 171 ± 15 | 145 ± 11 |
| Total lipid | 668 ± 146 | 610 ± 115 | 580 ± 104 | 570 ± 76*[1] | 582 ± 80 | 340 ± 36 |
| Lipid peroxides | 18 ± 5 | 17 ± 4 | 14 ± 4*[1] | 17 ± 3 | 14 ± 4*[1] | 26 ± 5 |

Each value represents the mean ± S.D. Significant difference of the test substance compared to the control group
*[1] $p < 0.05$,
*[2] $p < 0.01$, n = 8 – 17.

[Test Example 2] Effect of the present compound on streptozotocin-induced hyperlipidemia in rats

TABLE 2

| Group | Control | EPC-$K_1$ | | Probucol | Normal |
|---|---|---|---|---|---|
| Dose (mg/kg) | group | 125 | 250 | 125 | group |
| Triglycerides | 292 ± 95 | 195 ± 75*[1] | 192 ± 76*[1] | 191 ± 81 | 153 ± 23 |
| Total cholesterol | 63 ± 7 | 60 ± 5 | 64 ± 7 | 55 ± 5 | 61 ± 5 |
| Free cholesterol | 14 ± 6 | 10 ± 2 | 12 ± 3 | 10 ± 2 | 12 ± 2 |
| Esterified cholesterol | 50 ± 6 | 50 ± 5 | 51 ± 8 | 45 ± 5 | 49 ± 3 |
| HDL (%) | 89.0 ± 4.8 | 95.0 ± 2.8 | 95.6 ± 0.7 | 86.2 ± 3.9 | 88.9 ± 4.4 |
| VLDL (%) | 5.5 ± 1.7 | 2.8 ± 1.8 | 2.5 ± 0.6*[1] | 9.2 ± 2.2*[1] | 7.0 ± 2.8 |
| LDL (%) | 5.5 ± 3.8 | 2.2 ± 1.2 | 1.9 ± 0.4 | 4.7 ± 2.0 | 4.1 ± 2.0 |
| HDL/LDL ratio | 253 ± 222 | 638 ± 438 | 524 ± 144 | 221 ± 104 | 290 ± 190 |

TABLE 2-continued

| Group | Control | EPC-K₁ | | Probucol | Normal |
|---|---|---|---|---|---|
| Dose (mg/kg) | group | 125 | 250 | 125 | group |
| β-Lipoprotein | 492 ± 168 | 327 ± 128 | 329 ± 133 | 327 ± 143 | 247 ± 37 |
| Lipid peroxides | 30.4 ± 1.6 | 29.4 ± 1.6*¹ | 24.4 ± 3.6*¹ | 30.0 ± 1.2 | 29.4 ± 2.3 |
| Free fatty acids | 3538 ± 1049 | 2370 ± 611*² | 2542 ± 785*¹ | 2794 ± 1015 | 915 ± 126 |
| Phospholipids | 164 ± 15 | 152 ± 15 | 155 ± 15 | 140 ± 14*¹ | 147 ± 10 |
| Total lipid | 553 ± 115 | 437 ± 93*¹ | 443 ± 92*¹ | 414 ± 94 | 392 ± 35 |
| Blood glucose | 599 ± 43 | 586 ± 46 | 585 ± 34 | 629 ± 17 | 171 ± 13 |

Each value represents the mean ± S.D. n = 8 − 7 Significant difference of the test substance compared to the control group
*¹ $p < 0.05$,
*² $p < 0.01$.

[Test Example 3] Effect of the present compound on Triton WR-1339-induced hyperlipidemia in rats The effect of the present compound given orally was evaluated in rats with Triton WR-1339-induced hyperlipidemia.

[Test substances]

EPC-K₁ 250 mg/kg (dissolved in distilled water)

Probucol 250 mg/kg (suspended in 0.54 CMC)

[Methods]

Triton WR-1339 (Nakalai Tesque) 100 mg/kg was injected into the tail vein of Wistar rats (6 weeks of age) to construct rat models of hyperlipidemia. Each test substance was administered orally 1 hour before administration of Triton WR-1339. Blood samples for biochemistry tests were collected 24 hours after administration of Triton WR-1339.

[Results]

The results are shown in Table 3. As seen from Table 3, the present compound at 250 mg/kg significantly lowered triglycerides (TG) and non-esterified fatty acid (NEFA) levels. On the other hand, probucol failed to produce declines in these parameters.

TABLE 3

| Group Treatment group (mg/kg) | Control group | EPC-K1 250 | probucol 250 |
|---|---|---|---|
| Triglycerides | 182 ± 36 | 120 ± 34*¹ | 164 ± 32 |
| Total cholesterol | 72 ± 14 | 83 ± 7 | 71 ± 7 |
| HDL-ch | 49 ± 15 | 56 ± 8 | 49 ± 6 |
| β-Lipoprotein | 213 ± 78 | 147 ± 66 | 190 ± 52 |
| LDL | 221 ± 34 | 183 ± 43 | 200 ± 37 |
| VLDL | 60 ± 42 | 33 ± 19 | 40 ± 28 |
| Free fatty acids | 709 ± 92 | 554 ± 96*¹ | 643 ± 41 |
| Phospholipids | 136 ± 18 | 130 ± 13 | 130 ± 14 |
| Total lipid | 426 ± 29 | 374 ± 41 | 400 ± 50 |
| Lipid peroxides | 24 ± 3 | 18 ± 5 | 27 ± 2 |

Each value represents the mean±S.D. n=6.

Significant difference of the test substance compared to the control group: *1, $p<0.05$.

[Example 1] Oral tablet

| | |
|---|---|
| EPC-K₁ | 100 mg |
| Lactose | 75 mg |
| Starch | 20 mg |
| Polyethylene glycol 6000 | 5 mg |

The above ingredients are mixed in the conventional manner to provide a tablet. Where necessary, the tablet may be sugar-coated.

[Example 2] injection

| | |
|---|---|
| EPC-K₁ | 200 mg |
| Mannitol | 5.0 g |
| Sodium hydroxide, 1N soln. | q.s. |
| Distilled water | To make 100 ml |
| pH = 6.5 | |

The above ingredients are mixed and filtered through a bacterial filter. The filtrate is aseptically distributed into a glass ampule, 5 ml per ampule, followed by sealing by fusion of the glass to provide an injection.

What is claimed is:

1. A method of improving lipid metabolism in humans by administering to a human a lipid metabolism improving effective amount of a compound represented by the formula

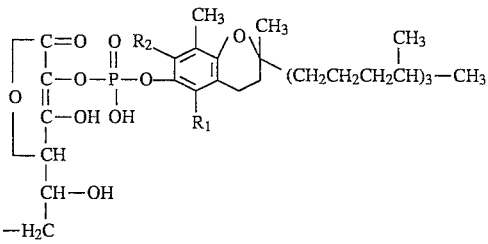

or a pharmacologically acceptable salt thereof, wherein $R_1$ and $R_2$ are the same or different and each represents a hydrogen atom or a methyl group.

* * * * *